United States Patent [19]

Swartz

[11] Patent Number: 4,775,365
[45] Date of Patent: Oct. 4, 1988

[54] LIPECTOMY CANNULA

[76] Inventor: Barry Swartz, 8070 Pimlico, Boerne, Tex. 78006

[21] Appl. No.: 100,084

[22] Filed: Sep. 23, 1987

Related U.S. Application Data

[63] Continuation-in-part of Ser. No. 907,505, Sep. 15, 1986, Pat. No. 4,735,605.

[51] Int. Cl.$^4$ ............................................. A61M 1/00
[52] U.S. Cl. .................................... 604/119; 604/248; 604/902; 137/625.22
[58] Field of Search ................... 137/625.22; 604/119, 604/902, 248

[56] References Cited

U.S. PATENT DOCUMENTS

| | | | |
|---|---|---|---|
| 312,155 | 2/1885 | O'Herin | 137/625.22 |
| 4,203,444 | 5/1980 | Bonnell et al. | 128/305 |
| 4,536,180 | 8/1985 | Johnson | 604/119 |

OTHER PUBLICATIONS

Body Contouring with Suction Lipectomy, by U. K. Kesselring, M.D., Clinics in Plastic Surgery, vol. 11, No. 3, Jul. 1984, pp. 393–417.

Primary Examiner—Carroll B. Dority, Jr.
Attorney, Agent, or Firm—Gunn, Lee & Jackson

[57] ABSTRACT

An improved lipectomy device, or cannula, is disclosed having inner and outer tubes. The outer tube has an elongated aspiration aperture, and the inner tube has a spiral slot. A mechanism inside the handle of the device causes the inner tube to rotate, creating a traveling hole effect along the aspiration aperture. This obviates the necessity of the surgeon repeatedly pushing the cannula in and out. A valve system is also disclosed which allows the surgeon to maintain negative pressure in the vacuum line leading to the cannula while still allowing the cannula itself to be vented to ambient pressures.

15 Claims, 3 Drawing Sheets

U.S. Patent    Oct. 4, 1988    Sheet 1 of 3    4,775,365
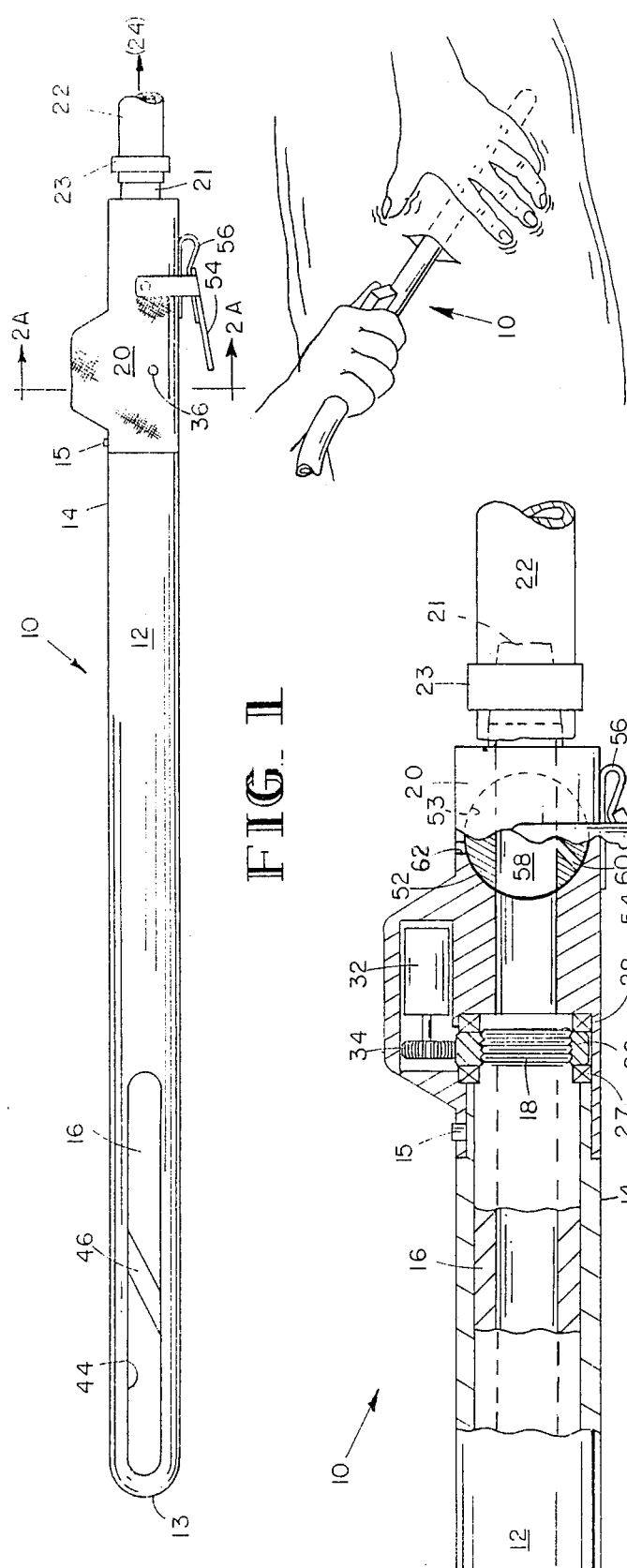

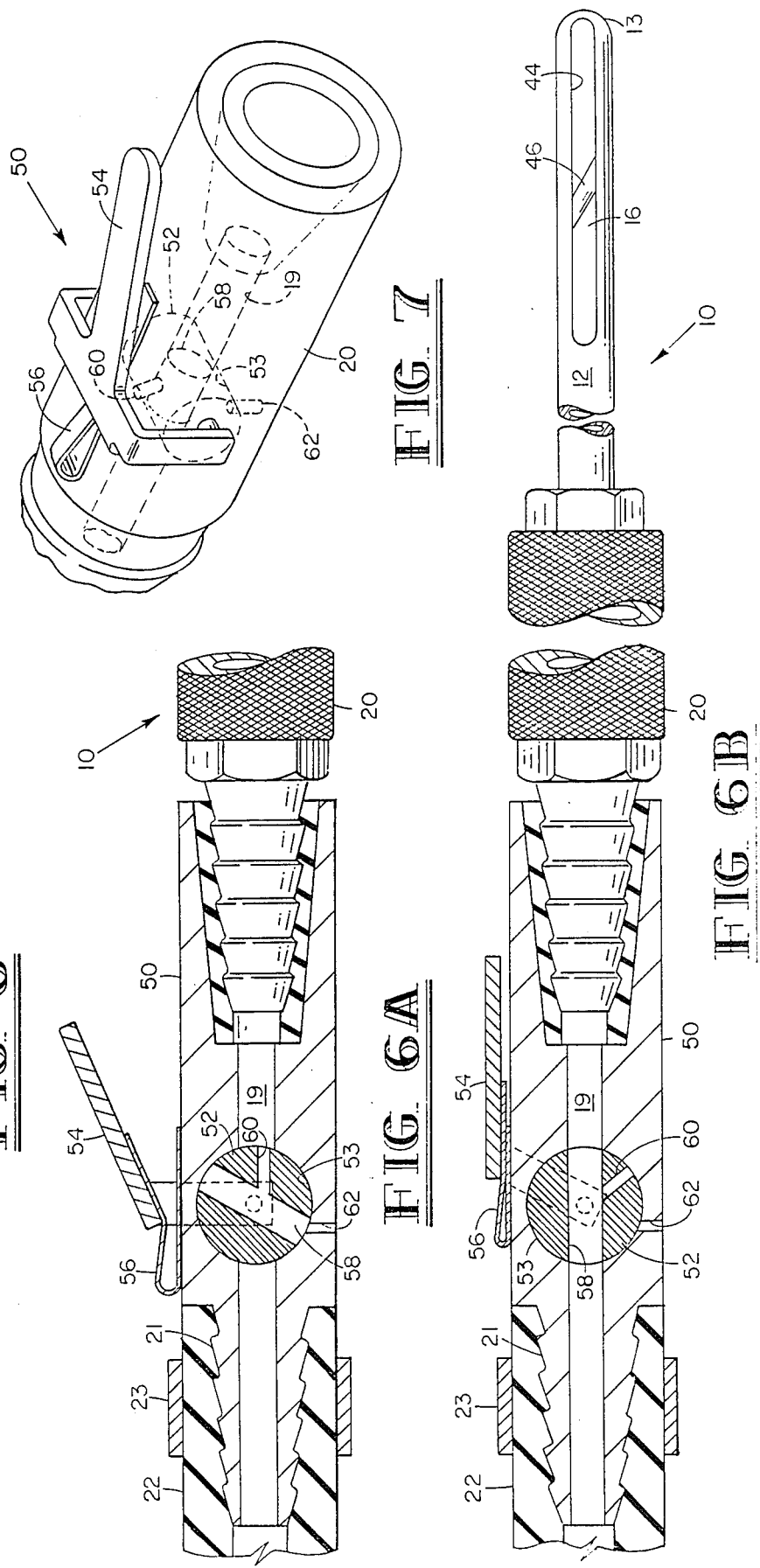

LIPECTOMY CANNULA

CROSS-REFERENCES TO RELATED APPLICATIONS

The present application is a continuation-in-part of U.S. patent application Ser. No. 907,505, now U.S. Pat. No. 4,735,605, for an Assisted Lipectomy Device, filed Sept. 15, 1986.

BACKGROUND OF THE INVENTION

1. Field of the Invention

The present invention relates to a lipectomy device for removing unwanted fat, and more particularly to an improvement in the vacuum system of such a device.

2. Description of the Prior Art

Body sculpturing, or body contour surgery, is a routine procedure used to increase the attractiveness of the human form. One particular technique of body sculpturing involves suction lipectomy, also known as liposuction or lipexheresis (Greek for "fat suction").

This technique was first used in Europe by J. Schrudde in 1972, who used a uterine curet for this purpose. Such a curet is depicted in U.S. Pat. No. 3,955,579, issued to Bridgman on May 11, 1976. An improved curet is shown in U.S. Pat. No. 4,311,140, also issued to Bridgman, on Jan. 19, 1982.

Although this technique was first created with some apprehension, it has now become widely accepted by both the medical community and by the layman. It can be practiced by physicians with different backgrounds, e.g., general practitioners, dermatologists, otorhinolaryngologists, or gynecologists, although it is most often performed by plastic surgeons. It has been used to remove fat from all over the body. The regions most frequently treated include the trochanteric region, flanks, buttocks, inner aspect of the knee, the anterior abdominal wall, gynecomastia, and "lovehandles." Although it was once believed that the fat cells so removed would later be replaced, the present accepted theory is that the body contains a limited number of fat cells that cannot regenerate. Fatty tissue is thus caused not by an increase in the number of fat cells, but by an increase in the amount of lipid matter found within the cell boundaries. Therefore, it is thought that removal of the fat cells by liposuction will create a contour that will retain its form.

Today the procedure is performed using a special type of curet known as a cannula. One excellent article discussing various shapes and sizes of cannulas is "Body Contouring with Suction Lipectomy" by Kesselring, published in Clinics in Plastic Surgery, Vol. 11, No. 3 (July 1984). One cannula often used is known as the Aspiradeps, manufactured by Ulrich A. G., in St. Gall, Switzerland. The cannula is attached to a vacuum source which carries away the fat tissue. The vacuum pressure is usually on the order of 0.4 to 0.6 atmospheres.

There are two accepted techniques practiced today. The first is the tunneling procedure proposed by Illouz. In this method, one or two incisions are made, with radial excursions of the instrument into the flesh. The result is a multitude of concomitant sinuses. The second, and most common method, is the original liposuction procedure proposed by Kesselring. In that technique, an entire layer of regular, deep fat is removed, leaving a smooth, deep surface of the residual panniculas. The space thus created is then compressed, optionally followed by skin retraction.

Both of these techniques require that the surgeon push and pull the entire cannula back and forth about twenty times for each incision made. Normally, twenty to thirty incisions, or tunnels, are made. This is necessary to insure even removal of fat in the targeted region. The surgeon typically massages the flesh in the area of the aperture in the cannula, while at the same time thrusting the rod in and out of the tunnel. This is an extremely traumatic method, both for the patient and the doctor. The patient's flesh turns black and blue for several days. Moreover, many surgeons practicing this techique find it physically exacting, and most come out of the operating room extremely tired.

Another problem relates to the amount of time required for the procedure. After the cannula has been inserted into the patient, the vacuum pump connected thereto is turned on. It may take up to a minute for adequate negative pressure to build up in the vacuum line before the surgeon can begin removal of fatty tissue. Then, each time the cannula is removed, the pump must be turned off, allowing the space within the cannula to equilibrate with ambient pressure. Otherwise, skin or other epidermal tissue may be damaged when the cannula is removed from the incision. It is extremely important to minimize the time necessary for the procedure as the patient is usually under general anesthesia, and prolonged exposure to anesthesia may result in serious consequences, such as an anaphylactic reaction. It would therefore be desirable and advantageous to devise an improved cannula which would assist the surgeon in the lipectomy procedure by decreasing the amount of time necessary to achieve a proper vacuum in the cannula, and also be decreasing the amount of time necessary for equilibrating the cannula with ambient pressure before removal.

SUMMARY OF THE INVENTION

Accordingly, the primary object of the present invention is to provide an improved lipectomy cannula which will assist the surgeon in the removal of fat from surrounding tissue.

Another object of the invention is to provide such a device which will reduce the time factor involved in creating the negative pressure required for suction lipectomy.

Yet another object of the invention is to provide a lipectomy cannula whose inner volume may be quickly vented to the surrounding atmosphere.

Still another object of the invention is to provide such a device which may be easily operated by the surgeon with the same hand that holds the cannula.

A further object of the invention is to provide a means of retrofitting existing cannulas to impart the aforesaid advantages.

The foregoing objects are achieved in an improved lipectomy cannula having a special valve on the handle thereof. A button or lever is depressed when negative pressure is desired, rotating the valve to provide fluid communication between the cannula and the vacuum source. When the lever is released, the valve rotates to its normally biased position which cuts off the cannula from the vacuum source, retaining negative pressure in the vacuum line, and providing a channel from the interior of the cannula to the exterior thereof.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed description of illustrative embodiments when read in conjunction with the accompanying drawings, wherein:

FIG. 1 is a side elevational view of the improved cannula of the present invention.

FIG. 2 is a partial cross-section of the cannula of the present invention showing the attachment of the inner and outer tubes to the gear assembly and handle.

FIG. 2A is a cross-section of the cannula of the present invention taken along lines 2A—2A of FIG. 1 showing an alternative gear assembly.

FIG. 3 is a partial cross-section of the cannula of the present invention showing the interaction of the spiral slot of the inner tube and the longitudinal slot of the outer tube.

FIG. 3A is a cross-section of the tip of the cannula taken along lines 3A—3A of FIG. 3.

FIG. 4 is a perspective of the improved cannula of the present invention depicting actual use of the device.

FIG. 6A is a cross-section showing the valve of the present system in its relaxed position.

FIG. 6B is similar to FIG. 6A, but the valve has been rotated to allow fluid communication between the cannula and the vacuum source.

FIG. 7 is a perspective view of the handle portion of the present invention showing the valve therein.

FIG. 8 is a perspective view of a cannula retrofitted with the valve of the present invention between the handle and vacuum hose.

DESCRIPTION OF THE PREFERRED EMBODIMENTS

Figure 5:
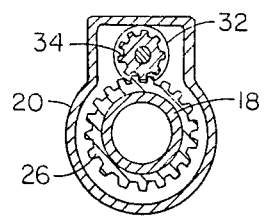
FIG. 5 is a front view of the drive and gear and tube gear arrangement shown in FIG. 2.

With reference now to the figures, and in particular with reference to FIG. 1, there is depicted a side view of the improved cannula 10 of the present invention. Improved cannula 10 comprises an outer tube 12, an inner tube 16, a handle 20, and a hose 22 leading to a vacuum source 24 (not shown). Cannula 10 may be any length up to 45 cm., but it generally depends on the location of the fat deposits. A 30 cm. cannula is preferred for the larger areas such as the buttocks, hips, and "saddlebags." A 10 cm. cannula is preferred for the knees, ankles, abdomen, and arms, and a 5 cm. or smaller cannula is required for the face. The diameter of the cannula is likewise variable, generally within the range of five to twenty-five millimeters. The distal end 13 of outer tube 12 should be slightly rounded or bullet-shaped. If the end were pointed or sharp, it might puncture vital organs or blood vessels within the body. If the end were totally flat, it would cause excessive damage to the fatty tissues. Handle 20 is preferably made of a resilient material, such a metal or hard plastic. Integral with handle 20 is port 21. Hose 22 is attached to port 21 by means of clamp 23, and should be made of a clear plastic.

With further reference to FIG. 2, it can be seen that inner tube 16 rotates within fixed outer tube 12 by means of a tube gear 26. The proximate end 14 of outer tube 12 is attached to handle 20 by means of a conventional twist and lock arrangement 15. The proximate end 18 of inner tube 16 is threaded and engages with inner tube gear 26. Tube gear 26 is held in place by bearings 27 and 28.

One advantage of this attachment method is the interchangeability of different sizes of inner and outer tubes. Although most cannulas today are made of surgical steel, it is envisioned that the outer and inner tubes 12 and 16 may be made of hard plastic or other easily manufactured material so as to make them disposable. The surface of water inner tube 16 may be coated with an anti-friction compound such a Teflon to ease the rotation thereof within outer tube 12.

Two alternate means of driving tube gear 26 are contemplated. The first, depicted in FIG. 2, includes an electric motor 32 housed within handle 20. Motor 32 would require a power cord (not shown) for connection to a source of electricity. Motor 32 powers drive gear 34 which in turn engages tube gear 26. Motor 32 may be activated by a thumb-operated on/off switch 36. Motor 32 may be air-driven instead of electric.

The second, and preferred, driving means is shown in FIG. 2A. This consists of a worm gear 38 engaged with tube gear 26. Worm gear 38 is powered by a rotating steel cable 40, located within a protective sheath 42. Cable 40 is powered by remote motor means, and controlled by a foot pedal (not shown). An example of such an arrangement is the cable system manufactured by Dermatomes for use with skin grafts. In this embodiment, element 36 may simply be a dimple for the thumb so that the operator is aware of the orientation of cannula 10.

Figure 3B:
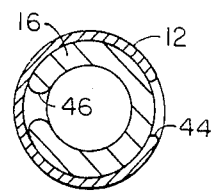
FIG. 3B is a cross-section of the cannula of the present invention showing the edges thereof.

With reference now to FIGS. 3 and 3A, it can be seen that both outer and inner tubes 12 and 16 are hollow. Outer tube 12 has a longitudinal slot 44 which generally corresponds to the aspiration apertures of the prior art cannulas. However, longitudinal slot 44 is much longer than those apertures. Although slot 44 may extend the entire length of outer tube 12, it is preferred, for reasons discussed below, that its length be approximately the width of a normal human hand, or about 8 cm., and being near the distal end 13 of outer tube 12. It should be at least 4 cm. long. The width of slot 44 should be between three and twenty millimeters, and preferably about 5 mm.

Inner tube 16 has a spiral slot 46 located near its distal end 17 so as to coincide with longitudinal slot 44 of outer tube 12. The effective length of spiral slot 46 should correspond to the length of longitudinal slot 44. Spiral slot 46 may make several revolutions around inner tube 16, but it is preferred that spiral slot 46 make only one 360° rotation along this length. Thereby, when inner tube 16 rotates, a "traveling hole" appears in longitudinal slot 44. The width of spiral slot 46 may be between three and twenty millimeters, preferably 12 mm. This feature obviates the necessity of the surgeon repeatedly pushing the cannula 10 to and fro, facilitating the entire operation and minimizing discomfort to the patient.

The direction of rotation of inner tube 16 should complement the threading of proximate end 18, so as to keep inner tube 16 engaged with tube gear 26. If proximate end 18 has right-handed male threads, the direction of rotation of inner tube 16 is counterclockwise as shown in FIG. 3A.

In the preferred embodiment, the edges of longitudinal slot 44 and spiral slot 46 are rounded rather than sharp. The functional differences between a rounded edge and a sharp edge are only apparent in the way in which the fat lobules are removed from their nutrient vessels. With the rounded edge, the fat lobules are torn off (avulsion) by the suction power across the edge of the slot, with minimal damage to the nutrient vessels; with a sharp edge, they are cut off (section) while being sucked into the tube. With the latter device, there exists a chance that the nutrient vessels themselves, or nerves or lymphatic tissue, may be cut, which is obviously undesirable. The fat wil then be conveyed down the center of inner tube 16, through cavity 19 in handle 20, and out port 21 and hose 22.

In an equivalent embodiment, the locations of the spiral and longitudinal slots could be reversed, placing the spiral slot on outer tube 12 and the longitudinal slot on inner tube 16. This approach, however, has certain drawbacks. First of all, the "traveling hole" would rotate around the cannula, making it impossible to concentrate on a given layer of fat. This would also result in excessive trauma to the surrounding tissue, and require a more powerful motor. Alternately, the inner tube may be similar to piston, and have an annular slot which would slide along the inside of the longitudinal slot.

With further reference to FIGS. 6A, 6B, and 7 a novel valve system 50 is disclosed, which is the subject of this continuation-in-part application. Valve system 50 resides in handle 20 of cannula 10, and is comprised of a rotating cylinder 52, a lever 54, and biasing means 56. The longitudinal axis of cylinder 52 is perpendicular to the axis of handle 20, and cylinder 52 is free to rotate therein. Cylinder 52 resides in a void 53, which bisects cavity 19 in handle 20 which leads to vacuum port 21. Cylinder 52 forms a threeway valve, and has a Y-shaped channel therein; the primary channel is designated as reference numeral 58, and the secondary channel is designated as reference numeral 60.

In FIG. 6A, biasing means 56 (which may simply be a clip spring) forces cylinder 52 to rotate in such a manner as to block the channel or cavity 19 leading to port 21. Cylinder 52 should fit tightly within void 53, and may be coated with some non-stick coating, such as TEFLON. Alternatively a gasket material (not shown) may be interposed between cylinder 52 and the inner surface of void 53. Also in FIG. 6, it can be seen that secondary channel 60 is in fluid communication with the distal end 13 of cannula 10. Secondary channel 60 leads to primary channel 58, which further leads to a vent hole 62. Thus, in its relaxed state, valve system 50 not only allows negative pressure to remain in the line leading to vacuum source 24, but it also allows the interior space of cannula 10 to equilibrate with ambient pressure.

FIG. 6B shows the orientation of valve system 50 while the cannula is actually being used to remove fat lobules. During use, the surgeon depresses lever 54, which causes cylinder 52 to rotate within handle 20. Rotation of cylinder 52 (clockwise going from FIG. 6A to FIG. 6B) brings primary channel 58 in alignment with cavity 19, providing negative pressure to cannula 10, and simultaneously seals vent hole 62.

Ideally, valve system 50 is manufactured integrally within handle 20 of cannula 10, but the system may be retrofitted to prior art cannulae. As shown in FIG. 8, valve system 50 may be attached to the end of vacuum hose 22 for direct coupling with port 21.

Although valve system 50 may be placed anywhere along vacuum hose 22, it is preferably placed as near as possible to cannula 10, for two reasons. First of all, by placing the system toward the distal end of hose 22, the amount of volume held at negative pressure is maximized. Thus the time required for generating a proper vacuum at slot 44 is minimized. Secondly, by placing the system near handle 20, the surgeon may activate the vacuum within cannula 10 using the same hand that is holding the device.

As those skilled in the art will appreciate, there are several alternative valve systems which may be used to carry out the intended functions of the present invention. For example, cylinder 52 may be electronically activated by switch 36, and rotated by means of a servo. Alternatively, the foot pedal used to engage motor 32 may also be used to activate rotation of cylinder 52. Cylinder 52 may be replaced by a spherical member performing the same function. Of course, use of valve system 50 is not limited to cannulas having inner tube 16. Standard curet-type cannulas may employ the valve system disclosed herein.

OPERATION

Existing procedures for preparing the patient for the lipectomy may be used in operations employing the improved cannula 10. The regions to be suctioned should be demarcated depending on the technique to be used. Anesthesia can be general, peridural, or local. The patient should be in either the prone or supine position depending on the targeted area. A saline or distilled water solution may be infiltrated in the fatty deposits.

An incision is made in the skin from 5 to 20 mm. in length depending on the diameter of the cannula. The device 10 is then inserted into the incision, creating a tunnel at the deep level of the tissue, near the fascia. This is necessary to avoid the lymphatics contained in the subcutaneous fat, and to retain skin trophicity and tonicity. The vacuum source 24 is then activated. A negative pressure of 0.3 to 1.5 atm, is required, depending on the size of the slots 44 and 46. It is anticipated that the optimum negative pressure for a cannula having an longitudinal slot width of 6 mm, and a spiral slot width of 12 mm. would be 1.0 atm. During vacuum buildup, cylinder 52 will be in the position shown in FIG. 6A.

When the cannula 10 is in place, the operator should activate the rotation of inner tube 16 by using the foot pedal, in the case of the preferred worm gear mechanism 38, or by depression of switch 36 in the case of the motor 32 within handle 20. At the same time, the operator should depress lever 54, causing cylinder 52 to rotate, providing a negative pressure at slot 44 of cannula 10. As depicted in FIG. 4, the operator should then begin to gently massage the region. The aspirated fat will be seen in hose 22. Fat is pure yellow, an if blood appears in the tubing the operator should change the orientation of cannula 10, or remove it. Filter units (not shown) may be attached to hose 22 before the vacuum source to keep track of the amount of fat and blood removed. After 100 cc. of fat have been removed, a new tunnel should be made and the procedure repeated. Lever 54 should be released before cannula 10 is withdrawn from the body. It is advisable to remove no more than six pounds of fatty tissue in order to avoid shock and other complications.

When the removal is complete, compression bandages should be applied. More than one operation may be necessary. Skin retraction may follow.

Although the invention has been described with reference to specific embodiments, this description is not meant to be construed in a limiting sense. Various modifications of the disclosed embodiments, as well as alternative embodiments of the invention will become apparent to persons skilled in the art upon reference to the description of the invention. It is therefore contemplated that the appended claims will cover such modifications that fall within the true scope of the invention.

I claim:

1. An improved lipectomy cannula, comprising:
   handle means;
   an outer tube having distal and proximate ends, and having a first longitudinal slot, said outer tube being open at said proximate end, and said proximate end of said outer tube attached to said handle means;
   an inner tube having distal and proximate ends, and having a second spiral slot, said inner tube located within said outer tube, said inner tube being open at said proximate end, and said proximate end of said inner tube attached to said handle means;
   vacuum means coupled to said inner tube for creating suction within said inner tube;
   said spiral and longitudinal slots each having rounded cutting edges along their length to remove fat lobules by tearing in conjunction with said vacuum means;
   motor means coupled to said inner tube for rotating said inner tube; and
   valve means having first and second positions whereby, when said valve means is in said first position, negative pressure is maintained within said vacuum means, and said inner tube is vented to surrounding atmosphere and, when said valve means is in said second position, said vacuum means is in fluid communication with said inner tube, said valve means being interposed between said inner tube and said vacuum means.

2. The improved lipectomy cannula of claim 1 wherein said valve means is located within said handle means.

3. The improved lipectomy cannula of claim 2 further comprising activation means for switching said valve means from said first position to said second position, and from said second position to said first position.

4. The improved lipectomy cannula of claim 3 further comprising means for biasing said valve means to said first position.

5. The improved lipectomy cannula of claim 3 wherein:
   said handle means has an extended cavity therein fluidly communicating said inner tube with said vacuum means;
   said handle means further has a cylindrical void therein, said void bisecting said cavity into distal and proximate portions, and adjacent to a vent hole in said handle means;
   said valve means includes a cylindrical member whose dimensions approximately equal the size of said void, said cylindrical member being rotatably mounted in said void, the axis of rotation of said cylindrical member being generally perpendicular to said extended cavity; and
   said cylindrical member further has primary and secondary channels therein forming a "Y", both of said channels being generally perpendicular to said axis of rotation of said cylindrical member, whereby when said cylindrical member is placed in a first orientation corresponding to said first position of said valve means, said secondary channel aligns with said distal portion of said extended cavity, said primary channel aligns with said vent hole, and said proximate portion of said cavity is obstructed, allowing said inner tube to equalize with ambient pressure while maintaining negative pressure in said proximate portion of said cavity and whereby, when said cylindrical member is placed in a second orientation corresponding to said second position of said valve means, said primary channel aligns with said extended cavity allowing fluid communication between said distal and proximate portions of said cavity, and said vent hole is obstructed.

6. The improved lipectomy cannula of claim 5 wherein said activation means comprises a lever member coupled to said cylindrical member whereby, when said lever member is moved, said cylindrical member rotates.

7. The improved lipectomy cannula of claim 6 further comprising means for biasing said lever member and said cylindrical member to said first orientation.

8. An improved lipectomy cannula comprising:
   a tubular member having first and second ends, for insertion into the fatty tissue of a patient, said tubular member having an opening at said first end;
   handle means having first and second ends and having a cavity extending therethrough, sadi first end of said handle means being connected to said second end of said tubular member, and said second end of said handle means having a port for attachment to a vacuum source, said port being in fluid communication with said cavity;
   valve means having first and second positions whereby, when said valve means is in said first position, negative pressure is maintained along a line connecting said port to said vacuum source and the inside of said tubular member is vented to surrounding atmosphere, and, when said valve means is in said second position, said vacuum source is in fluid communication with said handle means and said opening of said tubular member.

9. The improved lipectomy cannula of claim 8 wherein said valve means is located with said handle means.

10. The improved lipectomy cannula of claim 9 further comprising activation means for switching said valve means from said first position to said second position, and from said second position to said first position.

11. The improved lipectomy cannula of claim 10 wherein:
   said handle means further has a cylindrical void therein, said void bisecting said cavity into distal and proximate portions, and adjacent to a vent hole in said handle means;
   said valve means includes a cylindrical member whose dimensions approximately equal the size of said void, said cylindrical member being rotatably mounted in said void, the axis of rotation of said cylindrical member being generally perpendicular to said extended cavity; and said cylindrical member further has primary and secondary channels therein forming a "Y", both of said channels being generally perpendicular to said axis of rotation of said cylindrical member, whereby when said cylindrical member is placed in a first orientation corresponding to said first position of said valve means, said secondary channel aligns with said distal portion of said extended cavity, said primary channel aligns with said vent hole, and said proximate portion of said cavity is obstructed, allowing said tubular member to equalize with ambient pressure while maintaining negative pressure in said proximate portion of said cavity, and whereby, when said cylindrical member is placed in a second orientation corresponding to said second position of said valve means, said primary channel aligns with said extended cavity allowing fluid communication between said distal and proximate portions of said cavity, and said vent hole is obstructed.

12. The improved lipectomy cannula of claim 11 wherein said activation means comprises a lever member coupled to said cylindrical member whereby, when said lever member is moved, said cylindrical member rotates.

13. The improved lipectomy cannula of claim 12 further comprising means for biasing said lever member and said cylindrical member to said first orientation.

14. The improved lipectomy cannula of claim 8 wherein said valve means is located intermediate said port and said vacuum source.

15. An improved lipectomy device comprising:
a cannula having distal and proximate ends;
a handle having distal and proximate ends, and having a cavity extending therethrough, said distal end of said handle being attached to said proximate end of said cannula, said handle further having a cylindrical shaped void therein bisecting said cavity, and having a vent hole adjacent to said void;
a cylindrical three-way valve whose dimensions approximately equal the size of said void, said cylindrical valve being rotatably mounted within said void, the axis of rotation of said cylindrical valve being generally perpendicular to said cavity, and said cylindrical valve having primary and secondary channels therethrough forming a "Y", both of said channels being generally perpendicular to said axis of said cylindrical valve whereby said cylindrical valve may be placed in a first orientation wherein said secondary channel aligns with said cavity and said primary channel aligns with said vent hole, allowing said cannula to fluidly communicate with ambient atmosphere but obstructing fluid communication between said proximate end of said handle and said cannula, and further whereby said cylindrical valve may be placed in a second orientation wherein said primary channel aligns with said cavity allowing fluid communication between said proximate end of said handle and said cannula but obstructing said vent hole;
a lever coupled to said cylindrical valve and adjacent said handle for rotating said valve within said void; and
spring means for biasing said lever to a first position corresponding to said first orientation of said cylindrical valve.

* * * * *